United States Patent [19]

Gruenstein et al.

[11] Patent Number: 4,649,967

[45] Date of Patent: Mar. 17, 1987

[54] MULTIPLE EFFLUX APPARATUSES FOR TRANSFERRING FLUID

[75] Inventors: Eric I. Gruenstein; Richard T. Turner, both of Cincinnati, Ohio

[73] Assignee: University of Cincinnati, Cincinnati, Ohio

[21] Appl. No.: 770,018

[22] Filed: Aug. 29, 1985

Related U.S. Application Data

[63] Continuation of Ser. No. 530,371, Sep. 8, 1983, abandoned.

[51] Int. Cl.⁴ .............................................. G01N 1/14
[52] U.S. Cl. ................................... 141/59; 73/863.31
[58] Field of Search .............................. 141/7, 69, 65; 73/863.31, 863.32, 863.33

[56] References Cited

U.S. PATENT DOCUMENTS

| | | | |
|---|---|---|---|
| 2,784,748 | 3/1957 | Eichenlaub | 141/65 |
| 3,261,208 | 7/1966 | Fisher | 73/863.32 |
| 3,269,800 | 8/1966 | Lukrec | 422/65 |
| 3,327,535 | 6/1967 | Sequeira | 73/863.32 |
| 3,362,222 | 1/1968 | Johnson et al. | 73/863.31 |
| 3,811,484 | 5/1974 | Engelbrecht | 141/7 |
| 3,896,673 | 7/1975 | Audouze et al. | 73/863.33 |
| 4,231,989 | 11/1980 | Thoma | 422/63 |
| 4,244,042 | 1/1981 | Weinstein et al. | 435/30 |

FOREIGN PATENT DOCUMENTS

720161 12/1954 United Kingdom ............. 73/863.31

OTHER PUBLICATIONS

*Control Engineering,* "Flexible Bags Collect Gas Samples," p. 105, Sep. 1967.

*Primary Examiner*—Charles E. Phillips
*Assistant Examiner*—Mark Thronson
*Attorney, Agent, or Firm*—Wood, Herron & Evans

[57] ABSTRACT

Apparatuses and methods directed to transferring fluid from a supply container to a plurality of uptake containers are disclosed utilizing a common vacuum bore in communication with a plurality of channels adapted to receive the uptake containers for drawing vacuum in the uptake containers for delivery of fluid into the uptake containers. The apparatuses and methods further contemplate transferring a plurality of individual fluid samples, each contained in its own supply container, to a plurality of corresponding individual uptake containers in a one-to-one isomorphic displacement. Thus, the apparatuses and methods of this invention are capable of handling a large number of individual fluid samples in the shortest time possible without contaminating the homogeneity of the individual fluid samples being transferred. Additionally, the apparatuses and methods of this invention contemplate transferring fluid into a large number of samples in the shortest time possible. Further, the apparatuses and methods of this invention contemplate controlling the amount of fluid being collected.

12 Claims, 1 Drawing Figure

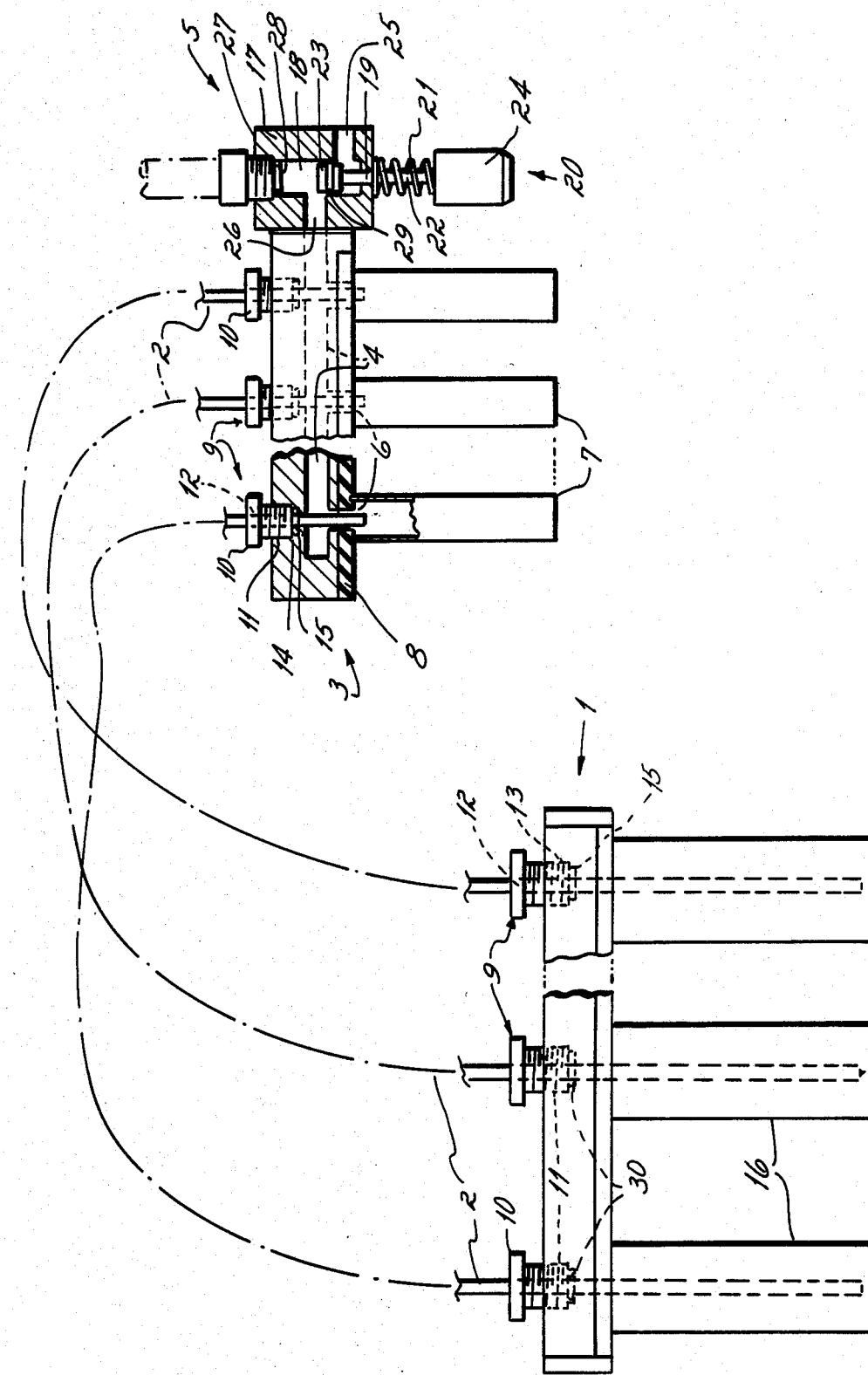

MULTIPLE EFFLUX APPARATUSES FOR TRANSFERRING FLUID

This application is a continuation of application Ser. No. 530,371, filed 9/8/83, now abandoned.

BACKGROUND OF THE INVENTION

Transferring numerous individual fluid samples or a large volume of fluid into numerous individual fluid samples in industrial and institutional laboratories for various diagnostic and research purposes has become standard procedure. Unfortunately, due to the number of samples or quantity of fluid being transferred, the procedure has become cumbersome and laborious. Devices known heretofore to assist the laboratory practitioners have been less than satisfactory in that they operate in a series of steps, they fail to maintain the homogeneity of individual fluid samples being transferred or they are complex and expensive. For instance, automatic pipetting machines, as disclosed in U.S. Pat. Nos. 3,337,535, 3,269,800 and 3,261,208, involve devices which draw vacuum upon supply containers to displace the fluid samples into uptake containers. There is additionally an automated flow system as disclosed in U.S. Pat. No. 4,245,042 wherein the homogeneity of individual fluid samples being transferred is sacrificed. Still further, there is disclosed in U.S. Pat. No. 4,231,989 a multi-channel system for handling immobilized substances in the shortest time possible. However, this device requires the use of a piston-cylinder unit connected to each container as a means to provide a vacuum source.

It is apparent from the above brief overview that there are commercial needs to provide apparatuses and methods that can handle a large number of individual fluid samples in the shortest time possible without interferring with the homogeneity, integrity, purity, and so forth, of the fluid samples being transferred.

SUMMARY OF THE INVENTION

The invention is directed to apparatuses and methods for transferring fluid from a supply container to a plurality of uptake containers. The apparatuses and methods comprise means for drawing a vacuum in a plurality of uptake containers for delivery of fluid into the uptake containers. The means may comprise, for example, a manifold having a common vacuum bore in communication with a plurality of channels for drawing a vacuum simultaneously in a plurality of uptake containers. The fluid may be transferred through separate transfer tubing from at least one supply container.

Thus, it is an object of this invention to provide apparatuses and methods to rapidly transfer fluid from a supply container to a plurality of uptake containers. Further, this invention contemplates transferring simultaneously a plurality of individual fluid samples each contained in its own supply container to a plurality of individual corresponding uptake containers in a one-to-one isomorphic displacement. Still further, this invention contemplates controlling the amount of fluid being transferred. The apparatuses and methods of this invention therefore are capable of handling a large number of individual fluid samples in the shortest time possible without contaminating the homogeneity of each transferred fluid sample. Further, the apparatuses and methods of this invention are capable of transferring a quantity of fluid into a large number of individual uptake containers in the shortest time possible. Pursuant to this invention, the term "fluid" as used herein comprises all substances having "flow properties" which can be employed to function with the apparatuses and methods of this invention.

These and other objects of this invention as well as its advantages will become apparent from the following detailed description, drawing and accompanying claims.

The FIGURE illustrates a side elevation of an apparatus made in accordance with this invention.

DETAILED DESCRIPTION OF THE INVENTION

As illustrated in the accompanying drawing, the apparatus comprises in combination a platform 1 connected by separate transfer tubing 2 to an integrally molded unit, e.g., a manifold 3, which has a common bore 4 connected to a valve assembly 5 which is connected directly to a vacuum source, not shown in the FIGURE. The common vacuum bore 4 is in communication with a plurality of channels 6 disposed in the manifold 3. The spacing of the openings in one end of the channels 6, in the manifold 3, are such that, when placed opposite a plurality of uptake containers 7, each opening of the uptake containers are fitted airtight around a corresponding opening of each said channel 6. To insure that an airtight fit is provided between the openings at one end of the channels 6 in the said manifold 3 and the open end of the uptake containers 7, a sealing substance 8, such as neoprene foam, may be affixed to the manifold 3.

There are additionally provided plug assemblies 9 which sealingly fit within the other open end of the channels 6 in the manifold 3 and the through ports 13 in the platform 1. The said plug assembly 9 may comprise a head 10 and a stem 11, or any other equivalent configuration, and a through going hole 12 through which a transfer tubing 2 is inserted. The transfer tubings 2 are preferably flexible. The stem 11 of the plug assembly 9 may be threaded to engage at one end of the channels 6 or at one end of the through ports 13 in the manifold 3 or the platform 1, respectively, a corresponding thread in the interior circumference of the channels 6 or the through ports 13 to provide an airtight fit. However, in keeping with this invention, the stem 11, or a like structure, may be fitted into one end of the channels 6 or the through ports 13 by other equivalent means as long as the fit is airtight.

Once the plug assembly 9 is inserted into the channels 6 or the through ports 13, one end of the stem 11 terminates at a seat 14 positioned adjacent to the common bore 4 in the manifold 3 or a seat 30 in the platform 1, wherein an O-ring 15 is provided which serves to sealingly receive the transfer tubing 2 and to provide an airtight fit between the plug assembly 9 and the seat 14 in the manifold 3 or the seat 30 in the platform 1. Upon tightening the inserted plug assemblies 9, the O-rings 15 are compressed constricting the holes and forming airtight seals around the transfer tubings 2. In addition, the depth of penetratin of the transfer tubings 2 into either the uptake containers 7 or the supply containers 16 may be individually adjusted and secured by loosening and retightening the plug assemblies 9. The plug assemblies 9 may be interchangeably compatible with the channels 6 in the manifold 3 and the through ports 13 in the platform 1.

As to the platform 1, a plurality of spaced through ports 13 are displaced therein. The spacing of the openings at one end of the through ports 13 in the platform 1 are such that when placed opposite a plurality of supply containers 16, each opening of the supply containers 16 are fitted at or around a corresponding opening of each through port 13. Unlike the manifold 3, an airtight fit is not necessary between the platform 1 and the supply containers 16. However, if an airtight fit is desired, the one end of the platform 1 may be provided with a sealing substance such as neoprene foam.

As to said valve assembly 5, it comprises in combination a housing 17 which has a common bore 18 having at one end an opening 27 for mounting a vacuum source and terminating in an end wall having an opening 19, and a piston 20 mounted to the housing 17. The piston 20 is resiliently mounted and more preferably spring mounted 21 and comprises a shaft 22 having a plunger 23 at one end and a handle 24 at other end for slidably extending through the end wall opening 19 along the central bore 18. The housing 17 further comprises a vent passageway 25 in communication with the central bore 18 and atmosphere. Additionally, the housing 17 further comprises a connecting passageway 26 disposed between the mounting end 27 of the central bore 18 and the vent passageway 25. The connecting passageway 26 communicates with the central bore 18 of the housing 17 and the common vacuum bore 4 of the manifold 3. In the central bore 18, a seat 28 is formed therein disposed between the mounting end 27 and the connecting passageway 26 for receiving the plunger 23 of the piston 20. The plunger 23 is provided with an O-ring 29 for sealingly sliding through the central bore 18 from the terminal end wall opening 19 of the central bore 18 beyond the venting passageway 25 and the connecting passageway 26 to the seat 28. Without departing from the spirit of this invention, the valve assembly 5 may be connected to the manifold 3 by any suitable means as long as an airtight fit is maintained between the central bore 18 of the housing 17 and the common vacuum bore 4 of the manifold 3. Additionally, the mounting end 27 of the central bore 18 may be connected to a vacuum source by any suitable means for securing an airtight fit between the housing 17 and the vacuum source. When the piston 20 is to be used, the plunger 23 of the piston 20 is made to selectively slide into a venting position wherein the central bore 18 and the common vacuum bore 4 are in communication with atmosphere by way of the venting passageway 25, an evacuating position wherein the central bore 18 is in communication with the common vacuum bore 4 by way of the connecting passageway 26, or a closing position wherein the communication between the central bore 18 and the common vacuum bore 4 is closed by the plunger 23. The evacuating position, being the preferred position, provides for simultaneously drawing a continuous vacuum in the plurality of uptake containers 7 by way of the common bore 4 for transferring fluid to the uptake containers 7. To maintain the vacuum in the uptake containers 7, but without draw, the plunger 23 is selectively moved into the closing position. To release the vacuum in the uptake containers 7, the plunger 23 is selectively moved into the venting position communicating atmosphere with the uptake containers 7. It should be understood, however, that any type of valve assembly may be used as long as it draws a vacuum to the common bore 4.

In its broadest aspect, the apparatus of this invention contemplates transferring fluid from a supply container 16 to a plurality of uptake containers 7 comprising means such as a manifold 3 for drawing a vacuum in a plurality of uptake containers 7 for delivery of fluid into the uptake containers 7 wherein the means comprises a common vacuum bore 4 for drawing the vacuum. In connection with the means are further means such as a valve assembly 5 for controlling vacuum in the common vacuum bore 4. Further, the apparatus provides for drawing a vacuum in a plurality of individual uptake containers 7 for simultaneously transferring fluid contained in a plurality of individual supply containers 16 to a a plurality of corresponding individual uptake containers 7. Thus, in the present embodiment, the apparatus enables large numbers of individual fluid samples to be simultaneously transferred in a one-to-one isomorphic displacement, i.e., supply container 1' transfers fluid to uptake container 1' in the shortest time possible while maintaining the homogeneity of each fluid sample being transferred.

In keeping with the broadest aspect of this invention, separate transfer tubings 2, preferably flexible, are connected airtight to the means and in communication with the vacuum for transferring fluid from a supply container 16 to a plurality of uptake containers 7. In another feature of this invention, one end of the separate transfer tubings 2 may be connected, preferably sealingly, to means such as a platform 1, for mounting the supply containers 16 while the other end may be connected sealingly to means, such as a manifold 3, for mounting the uptake containers 7.

In accordance with another preferred embodiment, this invention contemplates a method of transferring fluid from a supply container 16 to a plurality of uptake containers comprising means for drawing a vacuum simultaneously in a plurality of uptake containers 7 for collecting the transfer fluid in the uptake containers 7. As already discussed, the vacuum means may comprise a manifold 3 having a common vacuum bore 4 for drawing vacuum in a plurality of uptake containers 7. The fluid being transferred may be from a single supply container 16 or a plurality of individual supply containers 16. When the fluid is transferred from a plurality of individual supply containers 16, the homogeneity, integrity or purity of each sample being transferred is maintained. In addition, the methods provide for controlling the amount of fluid sample being collected.

Thus, the present apparatuses and methods of this invention are preferably designed to simultaneously transfer a large number of individual samples in the shortest time possible without contaminating the homogeneity of each fluid sample being transferred in a single step. Further, the apparatuses and methods of this invention contemplate transferring a fluid sample to a plurality of uptake containers in the shortest time possible. Still further, the apparatuses and methods of this invention contemplate controlling the amount of fluid sample being collected. The advantage is in the simplicity of construction of the apparatuses and their easy operation. Also, large numbers of individual fluid samples can be quickly and simultaneously transferred in basically one step. The necessity to draw the fluid samples up into a transfer device only to be released into a receiving container has been eliminated.

It is to be understood that the apparatuses and methods described herein may be varied at will so as to provide for the simultaneous transferring of fluid samples from any desired number of rows or parts of rows of supply and uptake containers. For instance, a plug may be designed to be inserted into each end of the channel 6 in the manifold 3 to inactivate that particular channel 6, as long as it does not interrupt the overall operation of the manifold 3. In keeping with the invention, the manifold 3, the platform 1 and the housing 17 all can be made of metal, glass, plastic or any other suitable material or combination thereof. Metallic or glass apparatuses are easily cleaned and sterilized, if required. Plastic apparatuses tolerate washing solutions which are corrosive to metals. The transfer tubings 2 preferably are flexible and may be made from, for example, polyethylene. The plug assemblies 9 may be made from any suitable material, such as polyethylene, which provides sufficient rigidity to form an airtight seal.

The present invention may, of course, be carried out in other specific ways than those herein set forth without departing from the spirit and the essential characteristics of the invention. The present embodiments are, therefore, to be considered in all respects as illustrative and not restrictive and all changes coming within the meaning and equivalency range of the appended claims are intended to be embraced herein.

What is claimed is:

1. An apparatus for transferring fluid from a supply container to a plurality of individual uptake containers comprising
    means adapted for drawing vacuum in a plurality of individual uptake containers for delivery of fluid into the uptake containers, said vacuum means comprises a common vacuum bore in communication with a plurality of channels in series having top and bottom ends for drawing the vacuum, the bottom end of each said channel being adapted for sealingly engaging an individual uptake container for communicating each individual uptake container with said vacuum means, each individual uptake container and said vacuum means being adapted for communicating with a supply container via separate transfer tubing having first and second ends, the first end of the transfer tubing being adapted to be received by a supply container and the second end of the transfer tubing being adapted to be sealingly received by the top end of one said channel for insertion therethrough and into a corresponding individual uptake container whereby, upon drawing a vacuum, fluid is transferred from a supply container through the separate transfer tubing into a plurality of individual uptake containers.

2. Apparatus of claim 1 further comprising a plurality of individual uptake containers and a plurality of corresponding individual supply containers for simultaneously transferring separate fluid samples to said uptake containers while maintaining the integrity of each of said separate samples.

3. Apparatus of claim 1 having additional means to control said vacuum in said common vacuum bore.

4. Apparatus of claim 1 wherein said vacuum means furthe includes a platform adapted for mounting the supply container, the separate transfer tubing being adapted for sealingly connecting said platform to said vacuum means to provide a continuous vacuum draw in each of the uptake containers and the supply container for simultaneously transferring the fluid from the supply container to the uptake containers.

5. Apparatus of claim 1 wherein each said channel is in communication with a corresponding supply container.

6. An apparatus adapted for transferring fluid from at least one supply container through transfer tubing to a plurality of uptake containers comprising:
    a platform having at least one through port, one end of said through port for sealingly receiving one end of said transferring tubing, said platform adapted for mounting a supply container at the other end of said through port;
    a vacuum means having a common vacuum bore and a plurality of channels in communication with said common vacuum bore, one end of each of said channels adapted to sealingly receive an end of said transfer tubing, said vacuum means being adapted for sealingly engaging uptake containers at the other end of said channel; and
    a valve assembly adapted to communicate with a vacuum source and said common vacuum bore, said valve assembly being adapted to selectively control the application of vacuum from a vacuum source for the purpose of transferring fluid from a supply container to uptake containers.

7. Apparatus of claim 6 wherein said channels are adapted to fittingly receive a plug assembly for securing and sealing airtight said transfer tubing between said vacuum means and said platform, said plug assembly comprising a plug having a head and stem movable within said channels.

8. Apparatus of claim 6 having further means for adjusting the position of said transfer tubing in said through port and said channels.

9. Apparatus of claim 7 wherein said vacuum means is integrally molded and is provided with neoprene foam for separately sealing airtight said uptake containers to said vacuum means.

10. Apparatus of claim 7 wherein said valve assembly comprises:
    a housing having a central bore, said central bore having a mounting end adapted for engaging a vacuum source, the other end of said central bore terminating in an end wall having an opening;
    a piston in said housing;
    a vent passageway formed in said housing communicating said central bore with atmosphere;
    a connecting passageway formed in said housing disposed between said mounting end of said central bore and said vent passageway, said connecting passageway communicating with said central bore and with said common vacuum bore; and
    a seat formed in said central bore disposed between said mounting end and said connecting passageway.

11. Apparatus of claim 10 wherein said piston is resiliently mounted onto said housing and comprises a shaft having a plunger at one end and a handle at other end, said shaft for slidably extending through said end wall opening, said plunger for sealingly sliding through said central bore from said terminal end of said central bore beyond said venting passageway and connecting passageway to said seat.

12. Apparatus of claim 10 wherein said piston is adapted to selectively slide into either a venting position, an evacuating position or a closing position, said venting position wherein said central passageway is in communication with said atmosphere, said evacuating position wherein said central bore is in communication with said common bore of said vacuum means, or a closing position wherein said communication between said central bore and said common bore of said vacuum means is closed by said plunger.

* * * * *

UNITED STATES PATENT AND TRADEMARK OFFICE
CERTIFICATE OF CORRECTION

PATENT NO. : 4,649,967

DATED : March 17, 1987

INVENTOR(S) : Eric I. Gruenstein and Richard T. Turner

It is certified that error appears in the above-identified patent and that said Letters Patent is hereby corrected as shown below:

Column 5, line 58, "wherein said vacuum means" should be deleted.

Column 5, line 59, "furthe" should be --further--.

Column 5, line 59, "includes" should be --including--.

Signed and Sealed this

Fifth Day of April, 1988

Attest:

DONALD J. QUIGG

*Attesting Officer*    *Commissioner of Patents and Trademarks*

UNITED STATES PATENT AND TRADEMARK OFFICE
CERTIFICATE OF CORRECTION

PATENT NO. : 4,649,967

DATED : March 17, 1987

INVENTOR(S) : Eric I. Gruenstein & Richard T. Turner

It is certified that error appears in the above-identified patent and that said Letters Patent is hereby corrected as shown below:

Col. 1, line 7, insert, before the Background of the Invention, --This invention was made with Government support under Grant No. NS-16287 awarded by the National Institutes of Health. The Government has certain rights in the invention.--

Signed and Sealed this

Eighteenth Day of January, 1994

Attest:

BRUCE LEHMAN

Attesting Officer　　　Commissioner of Patents and Trademarks